(12) United States Patent
Baumgart et al.

(10) Patent No.: US 8,150,125 B2
(45) Date of Patent: Apr. 3, 2012

(54) SYSTEM FOR VISUALIZING REGIONS OF INTEREST IN MEDICAL IMAGES

(75) Inventors: John Baumgart, Hoffman Estates, IL (US); Gary S. Martucci, Algonquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 740 days.

(21) Appl. No.: 12/260,501

(22) Filed: Oct. 29, 2008

(65) Prior Publication Data

US 2009/0110252 A1 Apr. 30, 2009

Related U.S. Application Data

(60) Provisional application No. 60/983,319, filed on Oct. 29, 2007.

(51) Int. Cl.
*G06K 9/36* (2006.01)
(52) U.S. Cl. ............ 382/130; 382/132; 378/98.12; 705/3
(58) Field of Classification Search ............ 382/130, 382/131, 132; 378/98.12; 705/2, 3
See application file for complete search history.

(56) References Cited

U.S. PATENT DOCUMENTS

| | | | |
|---|---|---|---|
| 6,052,476 A | 4/2000 | Qian et al. | |
| 6,380,740 B1 | 4/2002 | Laub | |
| 6,597,938 B2 | 7/2003 | Liu | |
| 6,628,743 B1 * | 9/2003 | Drummond et al. | 378/8 |
| 6,822,649 B1 * | 11/2004 | Schol | 345/440 |
| 6,894,707 B2 * | 5/2005 | Nemoto | 715/730 |
| 7,162,064 B2 * | 1/2007 | Klingenbeck-Regn | 382/131 |
| 7,203,353 B2 * | 4/2007 | Klotz et al. | 382/131 |
| 7,239,907 B2 | 7/2007 | Abe et al. | |
| 7,315,605 B2 | 1/2008 | Boese et al. | |
| 7,496,175 B2 * | 2/2009 | Sakaguchi et al. | 378/95 |
| 7,539,529 B2 * | 5/2009 | Schmitt et al. | 600/431 |
| 7,545,967 B1 * | 6/2009 | Prince et al. | 382/130 |
| 7,596,255 B2 * | 9/2009 | Mathew et al. | 382/130 |
| 7,616,799 B2 * | 11/2009 | Ramamurthy et al. | 382/131 |
| 7,715,519 B2 * | 5/2010 | Tsukagoshi et al. | 378/4 |
| 7,734,529 B1 * | 6/2010 | Zhou | 705/37 |
| 7,751,523 B2 * | 7/2010 | Ohishi | 378/4 |
| 7,835,496 B2 * | 11/2010 | Maschke | 378/91 |
| 7,949,170 B2 * | 5/2011 | Goto et al. | 382/131 |
| 7,974,682 B2 * | 7/2011 | Gonzalez Molezzi et al. | 600/432 |

* cited by examiner

*Primary Examiner* — Allen C. Ho
(74) *Attorney, Agent, or Firm* — Alexander J Burke

(57) ABSTRACT

A system for visualizing vascular fluid flow concentration includes at least one repository including a plurality of stored angiography scenes, an angiography scene comprises a plurality of individual images of a vascular structure successively acquired over a time period. A user interface control device enables a user to determine, (a) a duration and (b) a start time relative to a start time of the time period, of a window of interest within the time period. A control processor is electrically coupled to the user interface control device and the at least one repository. Control processor automatically assigns a unique visual indicator representing contrast flow of fluid through vessels to individual images within the user determined duration of the time period. A display processor, electrically coupled to the control processor and the user interface control device and at least one repository, generates data representing at least one display image comprising a composite image including individual images within the user determined duration of the time period having a unique assigned visual indicator.

24 Claims, 8 Drawing Sheets

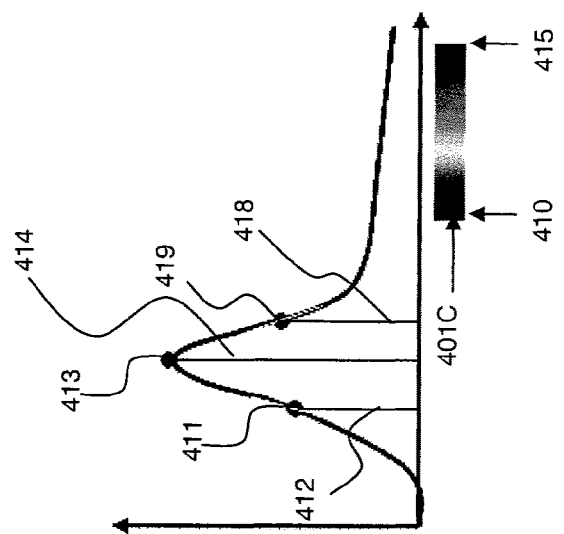
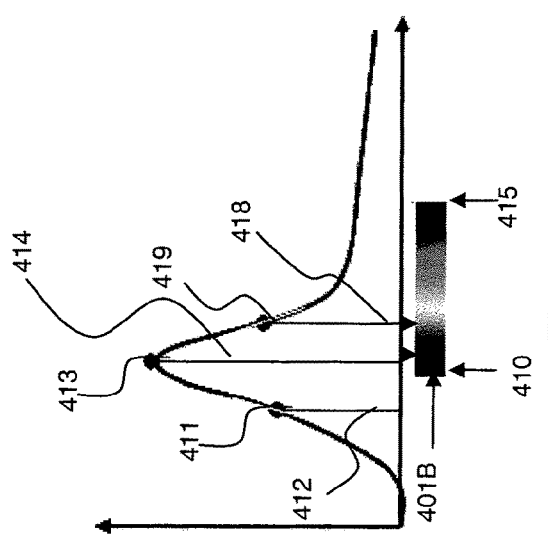
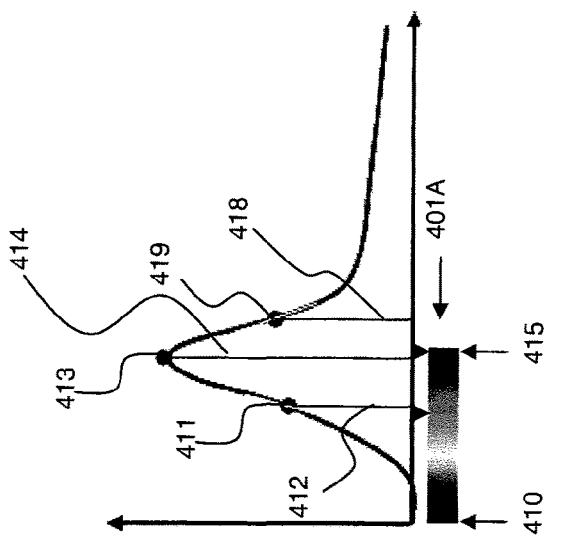
Fig. 4C
Fig. 4B
Fig. 4A

SYSTEM FOR VISUALIZING REGIONS OF INTEREST IN MEDICAL IMAGES

This is a non-provisional application of provisional application Ser. No. 60/983,319 filed Oct. 29, 2007, by John Baumgart et al.

FIELD OF THE INVENTION

This invention concerns a system for visualizing contrast flow of fluids through vessels during an angiography.

BACKGROUND OF THE INVENTION

X-ray angiography is performed to obtain an image of a vascular structure of a patient. An angiography enables a healthcare practitioner to obtain an image of particular blood vessels that supply blood to major organs such as the heart and brain, for example. Once obtained, the healthcare professional is able to review the flow of blood through the target vascular structures for diagnostic purposes. For example, angiographic images enable a healthcare professional to diagnose pathology of vessels such as blockage caused by plaque build up.

Angiographic x-ray imaging operates similarly to conventional x-ray in that x-rays are generated by an x-ray tube and as they pass through the body part being imaged, they are attenuated (weakened) at different levels. These differences in x-ray attenuation are then measured by a detector and the resulting image is recorded. The images are recorded successively thereby providing a series of moveable images able to viewed by the practitioner over time enabling the practitioner to evaluate the flow of blood through the target vasculature. The series of images, sometimes referred to as an angiography scene, are either viewed in real time on a display or stored for later review and evaluation. Angiography differs from conventional x-ray procedures in that during an angiography, a stream of contrast agent (dyes) is injected into the vessels to create detailed images of the vessels in real time.

Digital subtraction angiography (DSA) is a computer-aided image processing method used to enhance vasculature images in which each pixel of data acquired in an x-ray angiography procedure is digitized. DSA relies on the comparison between images taken immediately preceding an injection of a contrast bolus (mask image) and those obtained as the contrast bolus is passing through the target vessels (contrast image). The mask image is digitally subtracted from each of the contrast images resulting in the contrast-filled vessels being rendered on a display free of the background detail contained in the mask image. Additional known image processing functions for further enhancing the final images are performed to produce a series of successive images which are then replayed sequentially enabling a healthcare practitioner to visualize fluid flow through the target vessels.

When studying the contrast flow of fluid through vessels in an angiography scene, it is useful to build a static representation of the flow using a color spectrum to represent the time at which contrast reached a certain state within the vessels (e.g., first entered, reached a peak, no longer seen). However, a drawback associated with this type of visualization is that only a small time window of the entire acquisition may be of interest. A system according to invention principles addresses these deficiencies and related problems.

SUMMARY OF THE INVENTION

The inventors have advantageously recognized the need to provide a system enabling automatic control and adjustment of the time window while viewing the image and maintaining concentration on the appearance of the image. A system for visualizing vascular fluid flow concentration includes at least one repository including a plurality of stored angiography scenes, an angiography scene comprises a plurality of individual images of a vascular structure successively acquired over a time period. A user interface control device enables a user to determine, (a) a duration and (b) a start time relative to a start time of the time period, of a window of interest within the time period. A control processor is electrically coupled to the user interface control device and the at least one repository. Control processor automatically assigns a unique visual indicator representing contrast flow of fluid through vessels to individual images within the user determined duration of the time period. A display processor, electrically coupled to the control processor and the user interface control device and at least one repository, generates data representing at least one display image comprising a composite image including individual images within the user determined duration of the time period having a unique assigned visual indicator.

BRIEF DESCRIPTION OF THE DRAWINGS

FIGS. 4A-4C are graphical depictions of pixel intensity of a particular pixel over a length of an angiography scene according to invention principles;

DETAILED DESCRIPTION OF THE INVENTION

Figure 1:
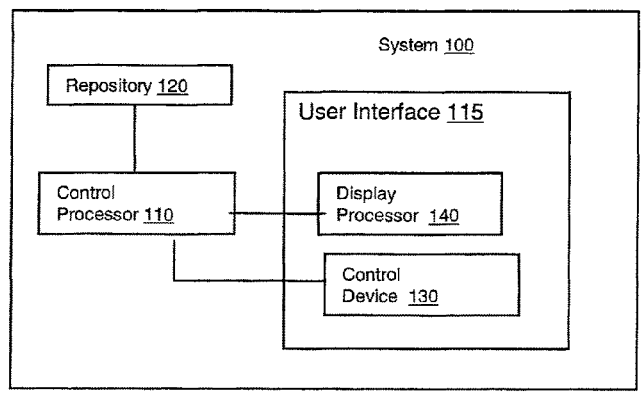
FIG. 1 is a block diagram of a visualization system according to invention principles.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

An embodiment of the system is shown in the block diagram of FIG. 1. The system 100 enables a user to control parameters used in creating a still image representing flow pattern of fluid (e.g. blood) through target vessels over a user specified time range. The still image created is derived from an angiography scene obtained from a patient and stored in a repository 120. As used herein, an angiography scene is a plurality of sequentially acquired individual image frames of target vessels in a patient. In an angiography scene, a contrast bolus has been injected through the target vessels and the flow pattern is visualized over time from image to image. System 100 is selectively controllable via a user interface 115. User interface 115 includes a display 140 enabling visualization of the selected angiography scene and a control device 130 for controlling the parameters used in producing a composite image representing fluid flow displayed on display 140. Control device 130 is a user manipulated device selectively moveable along at least two axis of motion. The control device includes, but is not limited to a mouse, touchpad, keyboard, directional control pad, joystick, light pen and touch-screen display interface. The multi-axis control device 130 enables a user to selectively and automatically modify a number of parameters equal to the number of axes over which the device is moved. For example, if the control device is moveable along two axes, the user selectively controls and modifies two different parameters. In one embodiment parameter modification occurs independently of one another. In another embodiment, first parameter modification is responsive to second parameter modification and vice versa.

User interface 115 enables user selection and modification of a first time parameter by moving the control device 130 along a first axis (e.g. x-axis). The first time parameter is a time width representing a range determined by the difference between a start time and end time of image acquisition that comprise the angiography scene. The user selectively moves the control device 130 along the first axis and automatically changes the value of the first time parameter. User interface 115 further enables selection and modification of a second time parameter by moving the control device 130 along a second axis different from the first axis (e.g. y-axis). The second time parameter is a value representing a midpoint (time center) of the first time parameter. Alternatively, the second time parameter is the starting time or ending time associated with the window of interest. For example, if the angiography scene has a total time of ten seconds and the control device 130 is moved to a point on the first axis whereby the time range equals six seconds, the second parameter value is automatically set to equal three seconds. Moving the control device 130 along the second axis, modifies the second parameter value by increasing or decreasing the point over time at which system 100 determines the center. Thus, the first time parameter is automatically modified in response to movement of the control device 130 along the second axis. In the event that the second parameter enables selection of start time or end time value for the window of interest to be visualized, movement along the second axis selectively modifies the value to be used. Additionally, system 100 enables a user to select and/or modify a third time parameter value different from the first and second time parameter values by moving the user interface control device 130 along a third axis, different from the first and second axis (e.g. the z-axis). The principles described with respect to movement along the first and second axis apply to movement of the user interface control device 130 along a third axis. Moreover, any number of directional movements may be incorporated enabling control over a number of parameters equal to the number of directional movement axis.

Control processor 110 is electrically coupled between user interface 115 and repository 120. While system 100 shows the components locally connected to one another, one skilled in the art will readily appreciate that components may be remotely located from one another and connected to one another by a communications network, such as the internet or a hospital network system connecting different hospital departments at different locations within a healthcare enterprise system. Control processor 110 receives control signals generated by user movement of control device 130 along either or both the first and second axis.

Operation of system 100 includes user selection, via user interface 115, of a particular angiography scene stored in repository 120. In response to selection, user interface 115 enables selection and creation of a static composite image detailing the contrast flow of fluid through the vessels depicted in the angiography scene according to two user-selected time parameters. Movement of control device 130 along the first axis to select and/or modify the first time parameter results in generation of a first control signal which is provided to control processor 110. The first control signal includes data representing points on the first axis corresponding to timestamps associated with individual images of the selected angiography scene. The first control signal is automatically and interactively updated and continuously provided in real-time to control processor 110 in response to user movement of control device 130 along the first axis. In response to first control signal, control processor 110 automatically assigns visual indicators according to a visualization scale to the individual images within the range determined by the first time parameter and provided in first control signal. The automatic assignment of a visualization scale occurs on a pixel by pixel basis such that a user is presented with a visual indicator for pixels comprising the individual images of an angiography scene. An exemplary method of associating the visualization scale with the particular image is discussed later in connection with FIG. 3. However, for purposes of FIG. 1, the assignment of the visual indicators according to the visualization scale is discussed in reference to as applied to individual images as a whole that comprise the angiography scene. The visualization scale includes visual indicators to assigned individual images at a respective time point within the selected time range as determined by the first time parameter. An exemplary visual indicator assigned by control processor 110 is a color spectrum gradient having a first color (e.g. red) associated with an imaging acquisition (or contrast agent introduction) starting time of the range determined in the first time parameter and a second different color (e.g. blue) associated with an ending time of the imaging acquisition range determined in the first time parameter. The use of red and blue as early and late color indicators is described for purposes of example only and because conventional angiography scenes utilize red color to indicate early blood flow and blue to indicate late blood flow. However, any color scheme may be utilized by system 100 so long as a different color or degree of color is associated with a particular image at a particular time. Individual images within the range determined by first time parameter that are between the starting and ending time points are further automatically assigned different unique colors. The visualization scale is displayed for example, as a legend within a display window and adjacent to the composite image showing fluid flow. Additionally, control processor 110 appends the visualization scale to data representing the time point within the selected range associated with the respective visual indicator. System 100 automatically assigns visual indicators to individual images within the range determined by first time parameter according to the visualization scale and advantageously enables a user to see a particular time point at which fluid represented by a particular color appearing in the vessel is flowing through the vessel.

Control processor 110, in response to selection of the first time parameter value, automatically sets a value of the second time parameter equal to a midpoint (or start or end time) of the range determined by the first time parameter value. The user is able to selectively modify the second time parameter value and change the images used in creating the composite image displayed on display 140, by moving the control device 130 along the second axis. Movement of control device 130 along the second axis shifts the time window to be displayed. Moving the control device 130 automatically modifies the second time parameter value and generates a second control signal including data representing points on the second axis corresponding to timestamps associated with individual images of the selected angiography scene. The timestamp data used in generating the second control signal define a midpoint (or start or end time) value to be used for a particular time range. Thus, by moving the control device 130 along the second axis, a user is able to shift the time window either forward or backward in the angiography scene while maintaining the selected duration of time determined by the range of the first time parameter. Upon shifting the time window being visualized, control processor 110 retrieves the respective images within the new time window and automatically adjusts the visual indicators used in the visualization spectrum to reflect the modified start time and end times. The automatic visualization ensures that the relevant contrast flow at the selected time is displayed enabling a user to focus on the fluid flow at that time period without having to determine and input the actual time of interest. System 100 also advantageously enables a user to use the data in the angiography scene to define a region of interest.

Figure 2A:
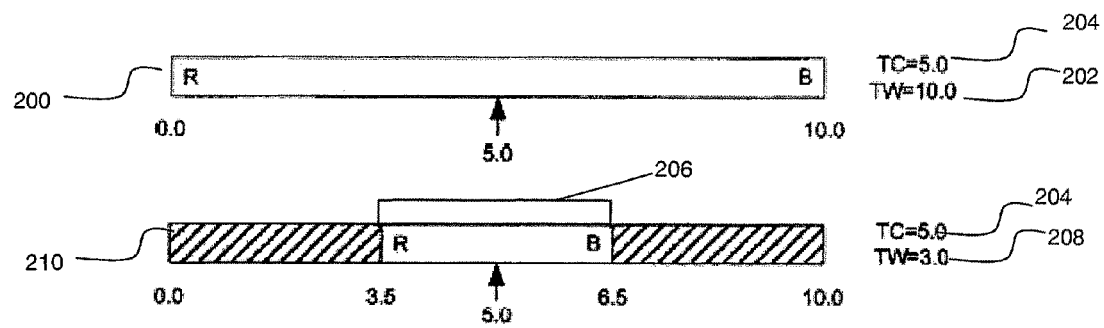
FIG. 2A is an illustration showing modification of a first time characteristic according to invention principles.
Figure 2B:
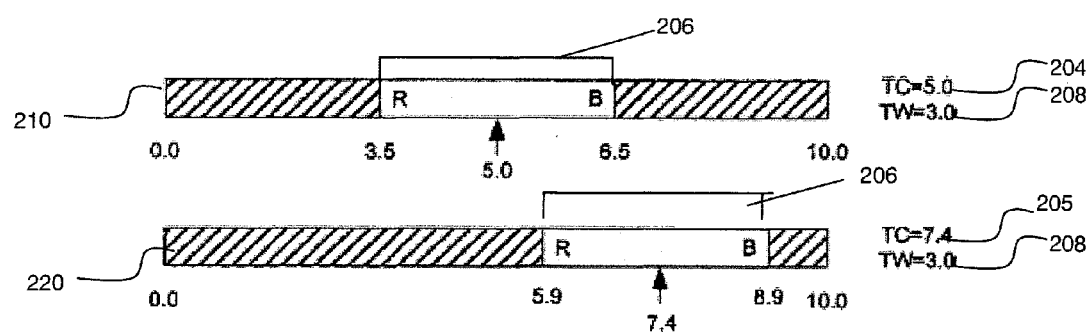
FIG. 2B is an illustration showing modification of a second time characteristic and an effect on the first time characteristic according to invention principles.

An exemplary operation of the user interface control of system 100 is shown in FIGS. 2A and 2B. FIG. 2A shows the effect of narrowing the first time parameter (time width) on the data displayed in the composite image. In this case, the entire dataset represents ten seconds, which is also the initial time width. When the width is reduced to 3 seconds, the data displayed will represent only the contrast that was seen in the window of interest having a start time of 3.5 seconds and an end time of 6.5 seconds. FIG. 2B illustrates the effect of shifting the second time parameter (time center) on the data displayed in the composite image. With the time width reduced to three seconds, shifting the time center to 7.4 seconds results in the data being displayed representing the contrast flow seen in the window of interest having a start time of 5.9 seconds and an end time of 8.9 seconds.

A user selects, via user interface 115, an angiography scene from repository 120 and control processor 110 automatically determines a total time value of the selected angiography scene and a midpoint of the total time value. The angiography scene selected by the user and shown in FIG. 2A has a total time of ten seconds (t=10) with a midpoint value of t=5 as shown by time bar 200. Thus, after initial selection the control processor 110 automatically assigns first time parameter 202 (time width) equal to total time and automatically assigns second time parameter 204 (time center) equal to t=5. Similarly, in time bar 210, in response to control device 130 being moved, system 100 generates the first control signal including a modified first time parameter 208 equal to a range of three seconds (3 s) and, in view of the second time parameter being unchanged at t=5, window of interest 206 having a duration of three seconds (3 s) is automatically determined to start when t=3.5 and end when t=6.5. Control processor 110 automatically assigns the visual indicators according to the visualization scale by associating the first visual indicator to the contrast flow image at time t=3.5 and further associating different visual indicators to contrast flow images at times t=3.5 through times t=6.5. Control processor 110 outputs a composite contrast flow image including the individual images within window of interest 206. Composite contrast flow image displayed on display 140 enables vascular differentiation by including the respective visual indicators associated with respective timestamps falling within window of interest 206 as determined by the first and second time parameters.

FIG. 2B provides an exemplary operation of system 100 in shifting the window of interest 206 along the length of time of the angiography scene by modifying the second time parameter 204. Time bar 210 is produced as described above in FIG. 2A. Time bar 220 illustrates the effect of shifting the window of interest 206 to a later point in the angiography scene. Control device 130 is moved along the second axis to define a modified second time parameter 205 including a midpoint value different from the originally assigned midpoint. As shown herein, second time parameter 205 is modified by moving control device 130 and determines midpoint value equal to t=7.4 s. As control device 130 was moved only along the second axis, the first time parameter value remains constant at three seconds (3 s). Control processor 110 automatically assigns the assigns the visual indicators according to the visualization scale by associating the first visual indicator to the contrast flow image at time t=5.9 and further associating different visual indicators to contrast flow images at times t=5.9 through times t=8.9. Control processor 110 outputs a composite contrast flow image including the individual images within window of interest 206. Composite contrast flow image displayed on display 140 enables vascular differentiation by including the respective visual indicators associated with respective timestamps falling within window of interest 206 as determined by the first and second time parameters.

In a further embodiment, control processor 110 automatically sets a value of the second time parameter in response to the first control signal. Moving control device 130 along the second axis results real-time modification of the second time parameter value and enables a user to automatically shift the window of images being visualized by modifying the midpoint from which the range in the first time parameter is calculated. By modifying the second time parameter, control processor 110 automatically, and in real-time, modifies the composite image being displayed on display 140 by reassigning visual indicators to the images that makeup the modified composite contrast flow image in the manner described above. For example, in an angiography scene having a total time of t=20, if a user moves control device 130 to a point on the second axis where t=15, control processor 110 automatically modifies first parameter value to maintain the duration of the selected range but modifies the start time to be equal to time t=5 and end at time t=25. Thus, the user is able to visualize the contrast flow of fluid through the vessels between times t=5 and t=25. In the event that second time parameter selected results in either start or end time of the range, determined by the first time parameter, exceeding or preceding the total time value of the angiography scene, control processor 110 automatically modifies the first time parameter value so as to not overrun the total time length of the angiography scene. Moreover, moving the control device 130 over both the first and second axis generates modified first and second control signals provided to control processor 110 which automatically recalculates the window of interest determined by the first and second time parameter values. In response to a recalculated window of interest, control processor automatically reassigns visual indicators according to the visualization spectrum to reflect the timestamps of the images within the recalculated window of interest. Thus, in response to moving the control device, system 100 displays composite contrast flow images that change in real-time. As the midpoint (center) and range (width of window being visualized) are adjusted, the newly represented time range is visualized using the entire visualization spectrum. Data that lies outside the specified time range is not shown. This advantageously allows the user to see flow over a user selected time period without having to know the exact time period at the time the static time-representative frame is generated.

In the preceding example, operation of system 100 is described by moving control device 130 along the first axis and subsequently along the second axis. However, it should be appreciated that a user may initially operate control device 130 along the second axis, thereby defining the second time parameter with a particular midpoint value. In this event, control processor 110 automatically assigns the first time parameter equal to total time of the angiography scene. Additionally, control device 130 includes a parameter lock switch enabling a user to lock a selected time parameter value and prevent further modification of the locked parameter value. In such an instance, that user is only able to further modify the other (non-locked) time parameter directly. However, if a respective parameter is locked and the selected time window is at either end of the allowable range for the time window, modifying the midpoint, start, or end of the window may result in the width changing as well so that it doesn't go past the end of the allowable time. An exemplary lock switch is a button on a joystick control device where the user maintains the button in a depressed position while moving the joystick over the other axis. Alternatively, the lock switch may be activated by a user depressing a key on a keyboard or a button on a mouse. These modes of locking a parameter in place are exemplary and one skilled in the art appreciates that many other modes of locking a parameter in place may be included depending on the type of control device 130 used with system 100.

Figure 3:
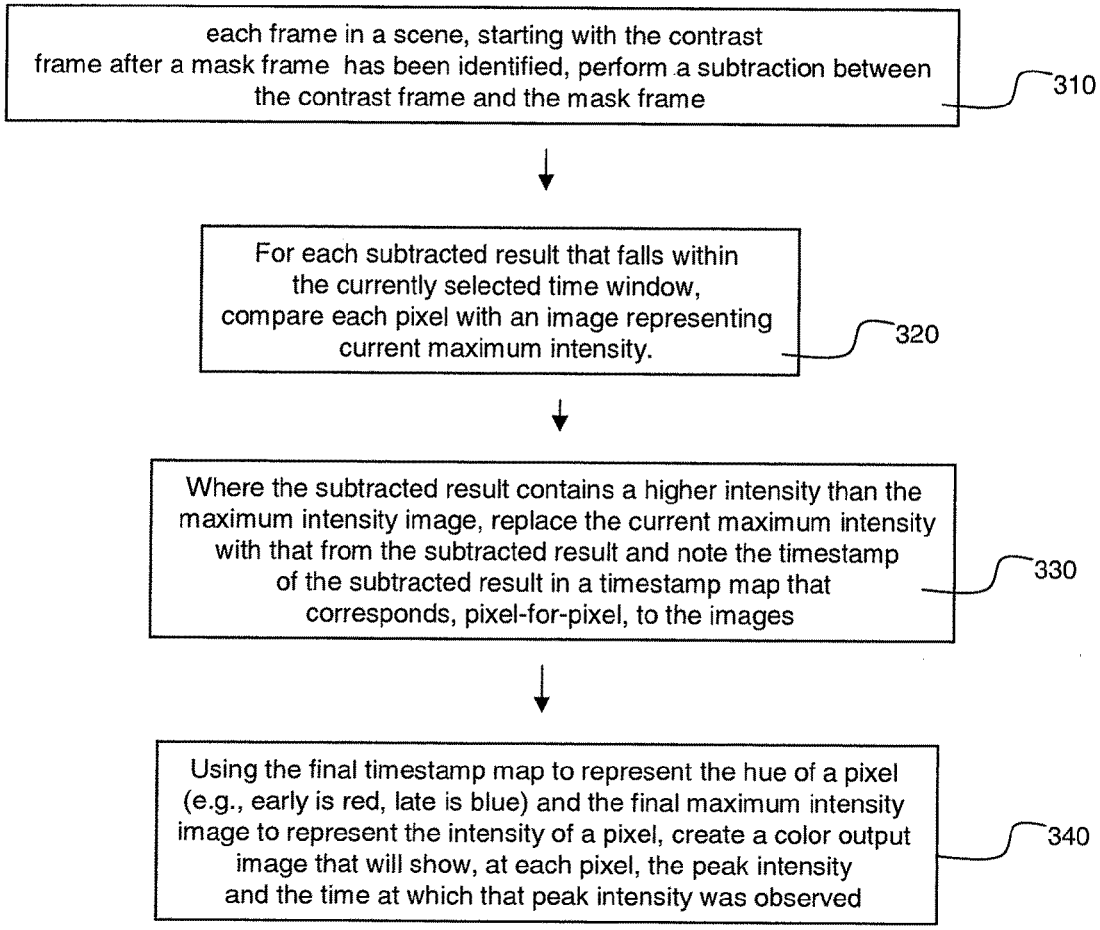
FIG. 3 is flowchart detailing an algorithm implemented by the visualization system according to invention principles.

FIG. 3 details an exemplary process performed in response to operation of control device 130 (FIG. 1) for selectively modifying at least one of the first and second time parameters. FIG. 3 illustrates applying visual indicators of the visualization scale to pixels that makeup the individual images of the angiography scene. For each individual image frame in an angiography scene, a mask frame and contrast frames are identified. Values representing luminance intensity data associated with the mask frames are subtracted from values representing contrast frame data as in step 310. In step 320, for each 0 subtracted result that falls within the currently selected time window of interest determined by first and second time parameter values, system 100 compares each pixel comprising the individual image with corresponding pixels in an image representing current maximum intensity. In step 330, where the subtracted result contains a higher intensity value than the maximum intensity image, system 100 replaces the current maximum intensity of the particular pixel with the value from the subtracted result and records the timestamp of the subtracted result in a timestamp map that corresponds, pixel-for-pixel, to the images. In step 340, a final timestamp map including pixel data for pixels in each respective individual image within the window of interest is used to represent the hue of a pixel with a particular visual indicator (e.g., early is red, late is blue) in conjunction with the final maximum intensity image to represent the intensity of a pixel. A composite contrast image is output and includes colors, at each pixel, indicating the peak intensity and the time at which that peak intensity was observed. Additionally, other known image processing techniques (e.g. normalization, gamma correction, etc) are applied to further enhance the composite image output by system 100.

FIGS. 4A-4C represent graphical views of pixel intensity calculated according to different intensity algorithms of a respective pixel over the duration of the angiography scene selected by the user. The x-axis of the graphs represent the time of the angiography scene where the origin represents time t=0 increasing to time t=n, where n represents the end time of the selected angiography scene. While not drawn to scale, the graphs in FIGS. 4A-4C have a start time of t=0 and an end time of t=20. The y-axis of the graphs depicts the contrast intensity being greater than a current maximum intensity image as described in step 330 of FIG. 3. Also shown is an exemplary window of interest depicted by the gradient bars 401A, 401B, 401C under the x-axis. The gradient bar 401A, 401B, 401C include a first color at a first end 410 representing the selected start time of the window of interest and successive different colors ending with a color at the selected end time 415 that is different than any other color previously used. Pixel intensity values 411, 413 and 419 shown in FIGS. 4A-4C representing intensity values calculated according to different algorithms that will be visualized for a single pixel within an angiography scene. However, at any given time, the value of 411, 413 or 419 will be displayed in the composite image produced by system 100 (FIG. 1). Point 413 represents the peak intensity value of the pixel at a specific point in an angiography scene. Point 411 represents the intensity value to be displayed that is calculated according to a maximum increase algorithm. Point 419 represents the intensity value to be display calculated according to maximum decrease. When the time window is adjusted such that a respective point is within the time window, the respective point is represented by the corresponding unique visual indicator (color and intensity). If the selected window of interest does not include a respective point (e.g. 413 in FIG. 4C), the point that contains the local maximum will have its intensity represented in the color corresponding to its position on the spectrum. For purposes of example, FIGS. 4A-4C will be discussed with reference to peak intensity pixel value at point 413. However, it should be appreciated that similar principles and applications apply to the values at either point 411 or 419 and the unique visual indicators displayed for those values correspond to the lines labeled 412 and 418, respectively.

FIG. 4A includes a window of interest 401A determined by a first time parameter value having a range of eight seconds (8 s) between t=0 and t=8. Additionally, peak intensity pixel value at point 413 is shown at time t=7.5 indicated by the line labeled 414. The visual indicator used to depict the peak intensity pixel value 413 (e.g. blue color) is different from other visual indicators used to depict any other pixel at different times.

FIG. 4B includes a shifted window of interest 401B. The visualization scale of the window of interest in FIG. 4B is the same as discussed above. The window of interest 401B is shifted in response to user modification of the second time parameter performed by moving the control device (130 in FIG. 1) along the second axis such that the second time parameter is set equal to t=11. This manner of shifting the window of interest is exemplary and is alternatively performed by modifying the second parameter which corresponds to a start time or end time of the window of interest. Shown herein, the first time parameter value defining the duration of window of interest 401B is maintained at 8 s. Thus, the start and end time is automatically adjusted by control processor (110 in FIG. 1) to start at t=7 and end at t=15. Peak intensity pixel value 413 is at time t=7.5 is depicted by the visual indicator (e.g. red color) associated with time t=7.5. Note that, due to the shifted window of interest 401B, the depiction of peak intensity pixel value 413 differs in color as compared to the depiction in FIG. 4A.

FIG. 4C includes yet a further shifted window of interest 401C. However, this respective pixel would not be depicted in any composite image produced from individual images within the window of interest 401C because the pixel intensity value is not greater than a value associated with a current maximum intensity value. The value at the beginning of this time window would be represented, by an indicator associated with the local maximum intensity value.

The graphical plots in FIGS. 4A-4C are for a single pixel. The process of associating individual pixels to respective visual indicators corresponding to time values within a window of interest are automatically performed for each pixel in real-time as the user moves the control device along the respective control axis. In the case of FIG. 4A, a bright blue pixel will be shown, for example while in FIG. 4B, a bright red pixel will be shown, for example. In both cases, this represents the same point in time for that pixel. In FIG. 4C, a dim red pixel will be shown, representing the intensity at the time corresponding to 410, since that is the local maximum along the curve. Should a user wish to visualize different intensity values calculated according different algorithms, the visual indicators display will differ. If a "maximum increase" algorithm is desired, then value 411 will be represented as cyan in FIG. 4A, a time just before that of value 413 will be represented in bright red in FIG. 4B, and as there is no increase in FIG. 4C, no value would be shown. Any algorithm for calculating pixel intensity may be implemented by system 100, for example in step 330 of FIG. 3.

Figure 5A:
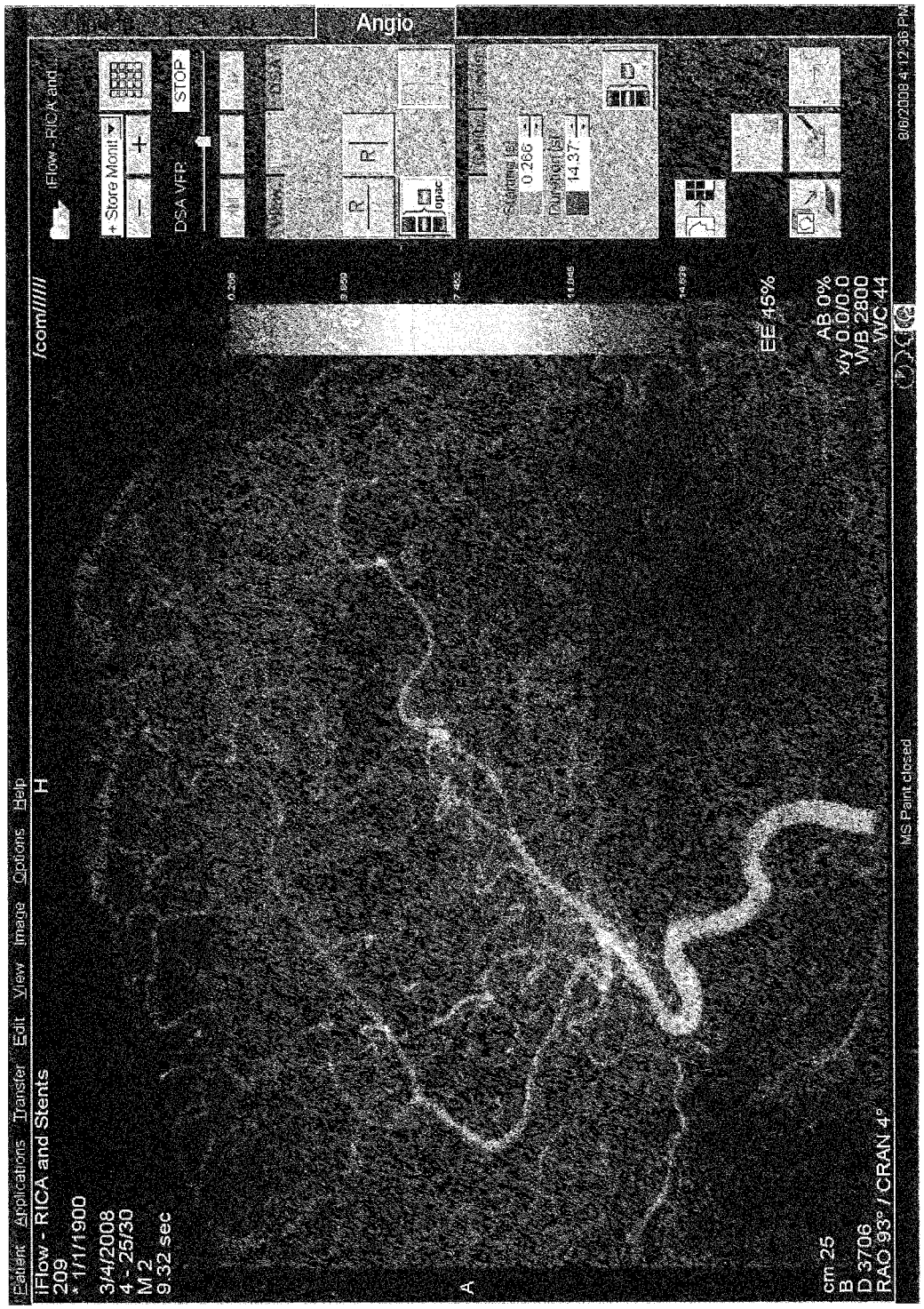
FIGS. 5A-5D are exemplary screen shots of the user interface of the visualization system according to invention principles.
Figure 5B:
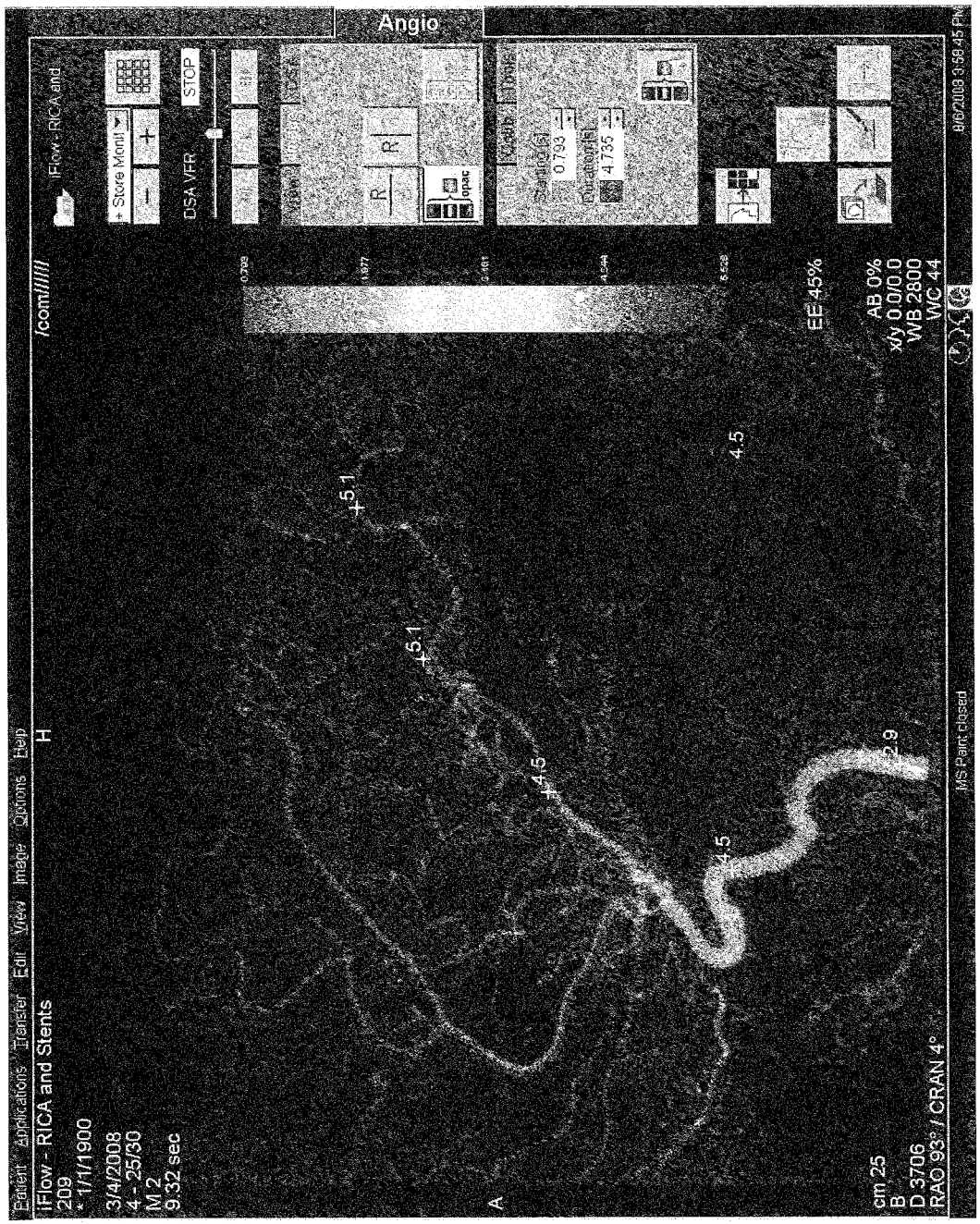
Figure 5C:
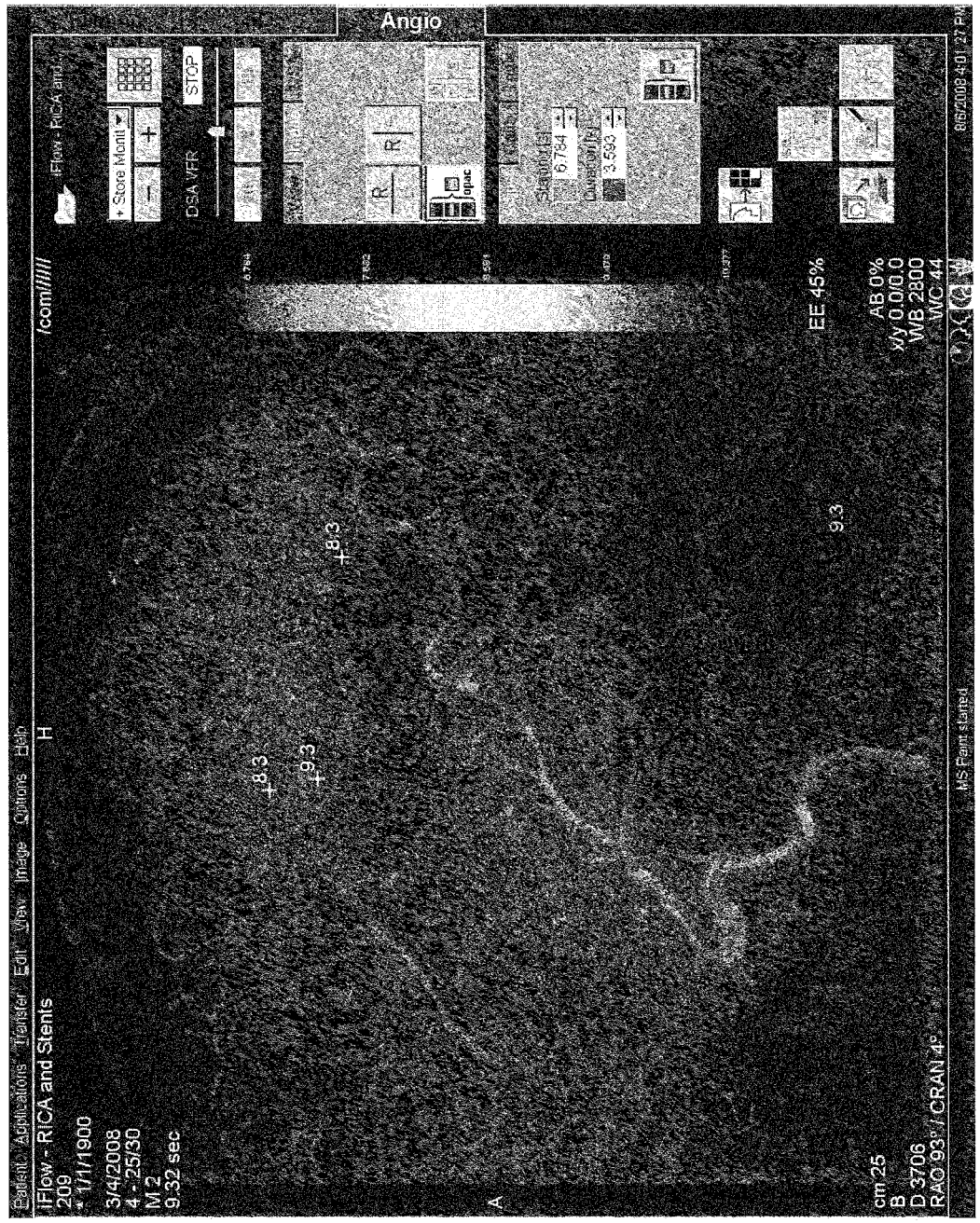
Figure 5D:

FIGS. 5A-5D are exemplary screen shots of the composite images produced by system 100 (FIG. 1) and output to display 140 (FIG. 1). The images shown herein show the contrast flow of fluid at varying time points of an angiography scene. Each screen shot includes a visualization legend including a color gradient bar defining the color used as the visual indicator at a particular time point and predetermined time values adjacent their respective color indicator to further improve the ease at which the user can select a desired window of time using the multi-axis control device 130 (FIG. 1). FIG. 5A is a composite display image showing contrast flow over the entire length of the selected angiography scene. The first time parameter, time width, is equal to the total time length of the angiography scene and is set equal to 14.37 s and selected to start at 0.266 s. In FIG. 5B, the first time parameter (time width) has been modified. Modification of the first time parameter in FIG. 5B occurs by moving the control device 130 along the first axis to a point on the first axis defining the first time parameter as 4.73 s and includes a start time at 0.793 s. In response to modification of the first time parameter using the control device, the composite image displayed in the exemplary screen shot differs from the image in FIG. 5A. Additionally, the visualization legend in FIG. 5B is automatically modified by control processor 110 to reflect to change in the first time parameter and the colors used as visual indicators are the same, the colors are associated with different time points within the window of interest. The composite image in FIG. 5B shows, for example the arterial flow of blood. The composite image shown in FIG. 5C is produced in response to further modification of the first time parameter to have a width of 3.593 s and a start time value of 6.784 s. Modification of the first time parameter as in FIG. 5C is performed in a similar manner as discussed above. Thus, the composite image in FIG. 5C depicts the contrast flow during the capillary phase. FIG. 5D includes a composite image representing venous blood flow which is produced in response to the first time parameter being modified as described above to have a time width value of 3.68 s but a starting time value at 10.95 seconds. The images in FIGS. 5A-5D described as being produced by a modification of the first and second time parameters are merely exemplary. The images are produced by moving the control device along a combination of first and second axis as the composite image is dynamically automatically produced by the control processor upon receipt of first and/or second control signals including data representing first and/or second time parameter values.

A further embodiment of system 100 enables visualization vascular fluid flow concentration within vessels and includes at least one repository including a plurality of stored angiography scenes. An angiography scene includes a plurality of individual images of a vascular structure successively acquired over a time period. A user interface control device enables a user to determine duration and a start time relative to a start time of the time period, of a window of interest within the time period. Additionally, user interface control device enables determining a midpoint value of the window of interest. User interface control device includes any (a) mouse, (b) touchpad, (c) keyboard, (d) directional control pad, (e) joystick, (f) light pen, (f) touch-screen display interface (g) an control device operated in response to voice command, (h) a proximity or motion sensing apparatus that does not require direct physical contact by a user and a capacitance sensor for sensing finger position relative to a sensor. A control processor is electrically coupled to the user interface control device and the at least one repository for automatically assigning a unique visual indicator representing contrast flow of fluid through vessels to individual images within the user determined duration of said time period. A display processor is electrically coupled to the control processor and the user interface control device and the repository, for generating data representing at least one display image comprising an individual image within the user determined duration of the time period having a unique assigned visual indicator. In this embodiment, the unique visual indicator is color, shade or hue and the individual images within the user determined duration are assigned a different color, shade or hue from other images. Additionally, display processor generates data representing an image element enabling a user to navigate through images in the determined duration of the time period and view change in color, shade or hue between different images of the individual images. The control processor also automatically associates at least one of (a) value representing blood flow velocity and (b) a volume representing blood flow volume, with said unique visual indicator.

Figure 6:
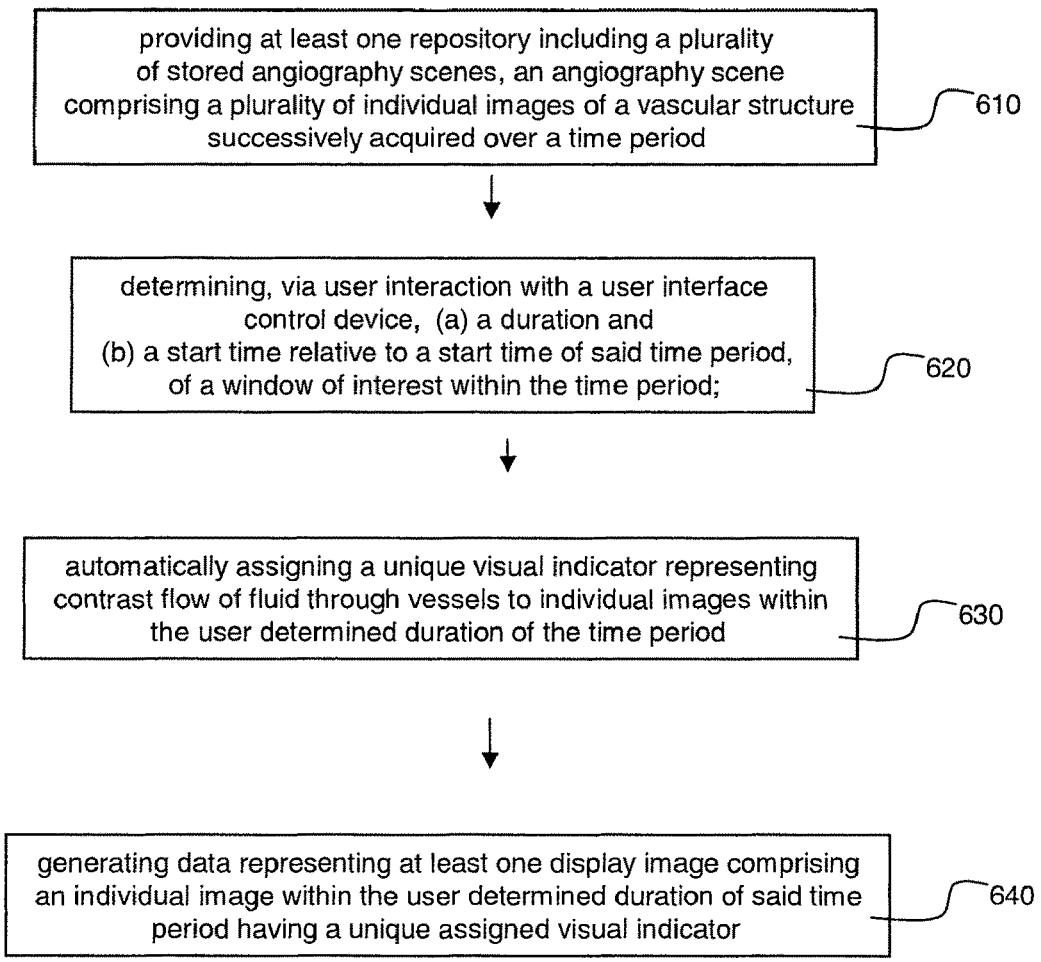
FIG. 6 is a flowchart detailing an operation performed by the visualization system according to invention principles.

An exemplary process implemented by system 100 is described in the flowchart of FIG. 6. System 100 provides a method for visualizing vascular fluid flow concentrations. In step 610, at least one repository is provided and includes a plurality of stored angiography scenes, an angiography scene comprising a plurality of individual images of a vascular structure successively acquired over a time period. In step 620, in response to user interaction with a user interface control device, duration and a start time relative to a start time of the time period, of a window of interest within the time period is determined. A unique visual indicator representing contrast flow of fluid through vessels is automatically assigned to individual images within the user determined duration of the time period in step 630. In step 640, data representing at least one display image comprising an individual image within the user determined duration of the time period having a unique assigned visual indicator is generated and displayed.

System 100 advantageously enables a user to narrow the duration of a window of interest in an angiography scene a specific phase of fluid flow through the vessels. Thus, by moving the control device along the first and/or second axis, the system automatically outputs composite images including the contrast flow of particular phases of blood flow starting with arterial, transitioning to capillary and then to venous flow. The multi-axis control device enables a user to concentrate on the flow during the time period without the need of knowing the precise time period of interest prior to visualization. This is particularly beneficial in treating and diagnosing arterial-venous malformations. These malformations generally present as a globule on a particular vessel. By moving the control device along the first and second axis, the user is provided with successive composite views enabling more precise diagnosis including which particular blood vessels are supplying blood to the malformation. These composite images are useable to narrow down and identify the vessels that need to treated in order minimize or remove the malformation.

The systems and processes described are not exclusive. Other systems and processes are derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIGS. 1-6. Further, any of the functions and steps provided in FIGS. 1-6 may be implemented in hardware, software or a combination of both and may reside on one or more processing devices located at any location of a network linking the elements of FIG. 1 or another linked network, including the Internet.

What is claimed is:

1. A system for visualizing vascular fluid flow concentration comprising:
   at least one repository including a plurality of stored angiography scenes, an angiography scene comprising a plurality of individual images of a vascular structure successively acquired over a time period;
   a user interface control device enabling a user to determine,
      (a) a duration and
      (b) a start time relative to a start time of said time period, of a window of interest within said time period;
   a control processor electrically coupled to said user interface control device and said at least one repository for automatically assigning a unique visual indicator representing contrast flow of fluid through vessels to each of the plurality of individual images within the user determined duration of said time period; and
   a display processor, electrically coupled to said control processor and said user interface control device and said at least one repository, for generating data representing at least one display image comprising an individual image within the user determined duration of said time period having a unique assigned visual indicator.

2. A system according to claim 1, wherein
said unique visual indicator comprises color, shade, or hue,
said at least one display image comprises a plurality of individual images, and
said individual images within the user determined duration of said time period are assigned a different color, shade, or hue from other images of said individual images.

3. A system according to claim 1, wherein
said at least one display image, which comprises a plurality of individual images, includes an image element enabling a user to navigate through images in said determined duration of said time period and view change in color, shade, or hue between different images of said individual images.

4. A system according to claim 1, wherein
said user interface control device enables determining duration in response to movement of said control device along a first axis.

5. A system according to claim 4, wherein
said user interface control device enables determining said start time relative to said start time of said time period in response to movement of said control device along a second axis.

6. A system according to claim 1, wherein
said control processor automatically associates at least one of (a) value representing blood flow velocity and (b) a volume representing blood flow volume,
with said unique visual indicator.

7. A system according to claim 1, wherein
said start time of said time period is relative to start of introduction of a contrast agent into the vascular structure, and
said user interface control device includes any of (a) mouse, (b) touchpad, (c) keyboard, (d) directional control pad, (e) joystick, (f) light pen, (g) touch-screen display interface, (h) a control device operated in response to voice command, (i) a proximity or motion sensing apparatus, and (j) a capacitance sensor for sensing finger position relative to the sensor.

8. A system according to claim 1, wherein
said user interface control device further comprises a parameter lock mechanism enabling a user to selectively lock at least one of said first time parameter value and a second time parameter value preventing modification of said locked parameter and enabling modification of an unlocked parameter value.

9. A system for visualizing vascular fluid flow concentration comprising:
at least one repository including a plurality of stored angiography scenes, an angiography scene comprising a plurality of individual images of a vascular structure successively acquired over a time period;
a user interface control device for determining a window of interest within an angiography scene, said user interface control device enables
selecting a first time parameter value, and
selecting a second different time parameter value;
a control processor electrically coupled to said user interface control device and said at least one repository for
selecting individual images from said at least one repository in response to said first and second time parameter values within said window of interest, and
automatically assigning a unique visual indicator to each of said selected individual images within said window of interest, the unique visual indicators corresponding to a time point within said window of interest; and
a display processor electrically coupled to said control processor, said at least one repository and said user interface control device for generating a composite display image including said unique visual indicators associated with said individual images within said window of interest representing a contrast flow of fluid through vessels.

10. A system according to claim 9, wherein
said first time parameter defines a duration of said window of interest and a start time within said angiography scene for said window of interest; and
said second time parameter defines a midpoint value of said window of interest.

11. A system according to claim 9, wherein
said first time parameter value is automatically modified in response to selecting said second time parameter.

12. A system according to claim 9, wherein
said second time parameter value is automatically modified in response to selecting said first time parameter.

13. A system according to claim 9, wherein
said user interface control device is selectively moveable along a first axis enabling selection of said first time parameter and along a second different axis enabling selection of said second time parameter.

14. A system according to claim 9, wherein
said control processor automatically assigns said unique visual indicators to individual images within said determined window of interest according to a visualization scale equal to a duration of the window of interest.

15. A system according to claim 14, wherein
said control processor automatically shifts a position of said visualization scale within the angiography scene in response to modification of at least one of said first time parameter value and a second time parameter value.

16. A system according to claim 9, wherein
said display processor automatically updates said generated composite display image in response to selecting or modifying said first and second parameter values.

17. A system according to claim 9, wherein
said user interface control device includes any of (a) mouse, (b) touchpad, (c) keyboard, (d) directional control pad, (e) joystick, (f) light pen, (g) touch-screen display interface, (h) a control device operated in response to voice command, (i) a proximity or motion sensing apparatus, and (j) a capacitance sensor for sensing finger position relative to the sensor.

18. A system according to claim 9, wherein
said unique visual indicator comprises color, shade or hue and
said individual images within a user determined duration of said time period are assigned a different color, shade or hue from other images of said individual images.

19. A method for visualizing vascular fluid flow concentration comprising the activities of:
providing at least one repository including a plurality of stored angiography scenes, an angiography scene comprising a plurality of individual images of a vascular structure successively acquired over a time period;
determining, via user interaction with a user interface control device,
(a) a duration and
(b) a start time relative to a start time of said time period, of a window of interest within the time period;
automatically assigning a unique visual indicator representing contrast flow of fluid through vessels to each of the plurality of individual images within the user determined duration of the time period; and
generating data representing at least one display image comprising an individual image within the user determined duration of said time period having a unique assigned visual indicator.

20. A method according to claim 19, wherein
the unique visual indicator comprises color, shade or hue and
further comprising the activity of assigning the individual images within the user determined duration of the time period a different color, shade or hue from other images of the individual images.

21. A method according to claim 20, further comprising the activity of
enabling a user to navigate through images using an image element in said at least one display image, in the determined duration of the time period and view change in color, shade or hue between different images of the individual images.

22. A method according to claim 19, wherein
the activity of determining a duration is performed by moving the user interface control device along a first axis.

23. A method according to claim 22, wherein
the activity of determining a start time relative to a start time of the time period is performed by moving the control device along a second different axis.

24. A method according to claim 19, wherein
the user interface control device includes any of (a) mouse, (b) touchpad, (c) keyboard, (d) directional control pad, (e) joystick, (f) light pen, (g) touch-screen display interface, (h) a control device operated in response to voice command, (i) a proximity or motion sensing apparatus, and (j) a capacitance sensor for sensing finger position relative to the sensor.

* * * * *